United States Patent

Nitsche et al.

[11] Patent Number: 5,902,890
[45] Date of Patent: May 11, 1999

[54] PROCESS FOR OBTAINING CAROTENE FROM PALM OIL

[75] Inventors: Michael Nitsche, Solingen; Wilhelm Johannisbauer, Erkrath; Volkmar Jordan, Steinfurt, all of Germany

[73] Assignee: Henkel Kommanditgesellschaft auf Aktien, Duesseldorf, Germany

[21] Appl. No.: 08/913,710

[22] PCT Filed: Mar. 11, 1996

[86] PCT No.: PCT/EP96/01040

§ 371 Date: Oct. 22, 1997

§ 102(e) Date: Oct. 22, 1997

[87] PCT Pub. No.: WO96/29306

PCT Pub. Date: Sep. 26, 1996

[30] Foreign Application Priority Data

Mar. 20, 1995 [DE] Germany .......................... 195 10 098

[51] Int. Cl.$^6$ ...................................................... C11B 7/00
[52] U.S. Cl. ............................................ 554/174; 554/195
[58] Field of Search ..................... 584/174, 195

[56] References Cited

U.S. PATENT DOCUMENTS

| | | | |
|---|---|---|---|
| 2,432,021 | 12/1947 | Larner | 167/81 |
| 2,460,796 | 2/1949 | Eckey et al. | 260/410.9 |
| 2,484,040 | 10/1949 | Lange et al. | 260/666 |
| 2,572,467 | 10/1951 | Gebhart | 260/236.5 |
| 2,652,433 | 9/1953 | Blaizot | 260/666 |
| 5,157,132 | 10/1992 | Tan et al. | 540/413 |
| 5,514,820 | 5/1996 | Assmann et al. | 554/167 |

FOREIGN PATENT DOCUMENTS

| | | |
|---|---|---|
| 39 32 514 | 4/1991 | Germany . |
| 0 691 924 | 5/1953 | United Kingdom . |
| 1 562 794 | 3/1980 | United Kingdom . |
| 2 218 989 | 11/1989 | United Kingdom . |

*Primary Examiner*—Gary Geist
*Assistant Examiner*—Deborah D Carr
*Attorney, Agent, or Firm*—Ernest G. Szoke; Wayne C. Jaeschke; Glenn E. J. Murphy

[57] ABSTRACT

Carotene is recovered from a native fat or oil in five process steps in an economical industrial process. The native fat or oil is catalytically reacted in known manner with an alkanol containing up to 4 carbon atoms to form fatty acid alkyl ester and glycerol. The ester phase of the reaction mixture is subjected to distillation to remove the fatty acid alkyl ester. The distillation residue obtained in the second process step is saponified, carotene is extracted from the product obtained in the third process step and the extract phase is concentrated by evaporation. A yield of at least about 80% is achieved. At the same time, a fatty acid alkyl ester suitable for further processing to fatty alcohol is provided.

25 Claims, No Drawings

PROCESS FOR OBTAINING CAROTENE FROM PALM OIL

This application is a 371 of PCT/EP96/01040 filed Mar. 11, 1996.

BACKGROUND OF THE INVENTION

1. Field of the Invention

This invention relates to a process for recovering carotene from a native fat or oil, more particularly from palm oil.

Depending on its origin, crude palm oil contains between 500 and 3,000 ppm of carotinoids containing a high proportion of beta-carotene and relatively low concentrations of tocopherols, tocotrienols and sterols.

Among the carotinoids, there are the oxygen-containing derivatives (xanthophylls) and the carotenes. The most well-known carotenes are alpha-, beta- and gamma-carotene and also lycopene. Beta-carotene occurs predominantly in nature and is the actual provitamin A. Since the carotenes are natural compounds and since they all show pronounced provitamin A activity, they are widely used as antioxidants or as dyes in commercial applications in the pharmaceutical industry, in the food industry and in the manufacture of cosmetics. More recently, the tumor-inhibiting activity of beta-carotene has been repeatedly demonstrated so that it is now also used in the prophylaxis of cancer.

2. Discussion of the Related Art

Several different processes for recovering carotene from palm oil or at least for concentrating carotene are known from the prior art.

In some known processes, the palm oil is first transesterified and/or saponified and then concentrated by extraction or distillation. Thus, according to U.S. Pat. No. 2,460,796, the palm oil is first transesterified with methanol. After the reaction mixture has settled out, the upper phase consisting of fatty acid methyl ester with dissolved carotene is washed with a mixture of alcohol and water and then with water alone. The complete or partial removal of the fatty acid methyl ester, which may be used for the production of soap, by distillation leaves a carotene concentrate. The distillation step is carried out in vacuo at temperatures of up to 150° C. The total distillation time mentioned in this document is around 5 hours.

The disadvantage of this known process lies in the high temperatures to which the heat-sensitive carotene is exposed and which rule out a high yield of carotene.

In another process known from U.S. Pat. No. 2,572,467, palm oil is first saponified (Examples I and II). Dilute sulfuric acid is added to the reaction mixture to obtain the corresponding free fatty acids. After settling, the fatty acid phase is dissolved in acetone and filtered. The filtrate is repeatedly cooled and refiltered to obtain a residue consisting of fatty acids and a carotene-containing solution from which carotene can be crystallized out at −70° C.

In a variant of this known process, transesterification with methanol replaces saponification of the palm oil with subsequent acid treatment (Examples III and IV of the same U.S. patent).

In a process described in U.S. Pat. No. 2,652,433, palm oil is subjected both to transesterification and to saponification. After neutralization and filtration, the crude palm oil is transesterified with methanol. Saponification of the ester phase is followed by an extraction step with petroleum ether or chloroform. The residue obtained after removal of the petroleum ether by distillation contains around 3% of carotene.

U.S. Pat. No. 5,157,132, which was published in 1992, discloses a process for concentrating carotene from palm oil which also begins with a transesterification step. The ester-rich phase obtained after settling is extracted with methanol and water to obtain a phase rich in carotene. Repeated extraction with methanol leaves a concentrated methanol/carotene mixture from which the alcohol is removed by evaporation in vacuo (Example I). In addition, the carotene-containing fatty acid methyl ester can be saponified after the transesterification step before it is extracted with petroleum ether. In this process, therefore, all the carotene-containing fatty acid methyl ester is saponified (Example II).

According to GB 2,218,989 A, the crude palm oil is subjected after transesterification with methanol to liquid chromatography with methanol and a mixture of hexane and methanol or chloroform as mobile solvent to obtain a fraction rich in carotene.

The disadvantage of extracting carotene from fatty acid methyl ester is that the fatty acid methyl ester is contaminated with the extractant which prevents the ester from being further processed by hydrogenation to fatty alcohol. In general, the ester obtained in this process cannot be put to any further use and has to be disposed of. The same disadvantage attends the extraction processes which start directly from palm oil without preliminary transesterification.

A process without this disadvantage is described in U.S. Pat. No. 2,432,021 where carotene is obtained in concentrated form by extraction with liquefied propane and subsequent rectification. Although, in this case, the palm oil can be subsequently used for the production of fatty alcohol, the process cannot be carried out economically on an industrial scale.

In addition, adsorptive processes for concentrating carotene are known from GB 691, 924, from GB 1,562,794 and from U.S. Pat. No. 2,484,040.

To summarize the prior art, it may be said that the known processes either cannot be economically carried out on an industrial scale or the yield of carotene is too low as a result of thermal and/or chemical decomposition or poor selectivity or that, after the process has been carried out the palm oil or the palm oil derivative is no longer suitable for the production of fatty alcohols.

DESCRIPTION OF THE INVENTION

Accordingly, the problem addressed by the present invention was to achieve a yield of at least about 80% in an economically workable industrial process for recovering carotene from a native fat or oil, more particularly palm oil, and at the same time to provide a native oil or oil derivative, for example an alkyl ester, suitable for further processing to fatty alcohol. Accordingly, the palm oil used would not be contaminated by the process according to the invention so that it would be suitable for further processing.

According to the invention, the solution to this problem is characterized in that 1. the native fat or oil is catalytically reacted (transesterified) in known manner with an alkanol containing up to 4 carbon atoms, more particularly methanol, to form fatty acid alkyl ester and glycerol,
2. the ester phase of the reaction mixture is subjected to distillation to remove the fatty acid alkyl ester,
3. the distillation residue obtained in the second stage of the process is reacted with a base, preferably potassium or sodium hydroxide (saponification), 4. carotene is extracted with a suitable solvent from the product obtained in the third stage of the process and, finally, 5. the extract phase is concentrated by evaporation.

It is possible by the process according to the invention to produce a carotene concentrate with a carotene content of 4 to 100% by weight, preferably 10 to 90% by weight and, more preferably, 18 to 70% by weight from a native fat or oil with a carotene yield of at least about 80%, based on the fat or oil used. At the same time, virtually the entire quantity of oil used is made available in the form of fatty acid alkyl ester for subsequent hydrogenation to fatty alcohol. Accordingly, besides the carotene concentrate and the glycerol obtained by transesterification, another useful material is obtained in the process according to the invention.

This is achieved by the above-mentioned removal of the alkyl ester by distillation from a carotene-containing residue and subsequent saponification and by limitation of the extraction step to the hydrolyzed distillation residue. The carotene yield of around 80% mentioned above is achieved despite the limitation of the extraction step to this part of the reaction mixture obtained from the transesterification step and despite the high temperatures required for the distillation step. It is also surprising that it is possible to remove up to 99% of the alkyl ester free from carotene despite the minimal different in vapor pressure between the alkyl esters and the carotene. Accordingly, there is also no need to purify the alkyl ester removed before it is hydrogenated to fatty alcohol.

Accordingly, the combination of removal of the ester phase by distillation and subsequent saponification of the distillation residue before extraction is crucial to the invention.

The free fatty acids present in the native fat or oil are preferably esterified before transesterification with the short-chain alkanol mentioned or are saponified during the transesterification step which, to this end, is carried out in the presence of a sufficiently large amount of alkaline catalyst.

The first step of the process according to the invention, i.e. the transesterification step, may be carried out in batches or even continuously in reactors of different kinds, for example in stirred tank reactors or tube reactors. One example of transesterification carried out in a tube reactor is described in DE 39 32 514 A1. Methanol, ethanol, n- or iso-propanol or -butanol may be used as the alcohol. Methanol is preferably used.

If an alkaline catalyst is used, it is preferably sodium hydroxide, potassium hydroxide, sodium methylate or potassium methylate.

Since carotene is extremely sensitive to heat, low reaction temperatures and short reaction times during the transesterification step are advantageous. A reaction temperature of 30 to 110° C. and, more particularly, 50 to 70° C. is proposed. The reaction time should be between 10 and 180 minutes and, more particularly, between 30 and 90 minutes.

A two-phase mixture is obtained on completion of the transesterification step. The lower phase consists of glycerol and does not contain any carotene. The upper phase essentially contains fatty acid alkyl ester, excess alcohol and the carotene present in the native oil used. The upper phase and lower phase are separated by decantation.

In the second step of the process according to the invention, the fatty acid alkyl ester obtained in the transesterification step is purified by distillation. To this end, it is proposed that 70 to 99.5% by weight and, more particularly, 95 to 99% by weight of the fatty acid alkyl ester obtained in the transesterification step be removed. Virtually all the fatty acid alkyl ester is separated from the carotene-containing residue in this step. The alkyl ester obtained in pure form is unconditionally available as a high-quality oleochemical starting material, for example for the production of fatty alcohols or technical esters. Another advantage is that the carotene remains entirely in the distillation residue and is considerably concentrated in this way. This results in a considerable reduction in the effort involved in the subsequent steps for further concentration.

The fatty acids of palm oil which consist predominantly of palmitic acid, stearic acid, oleic acid and linoleic acid have very long chains and require a low pressure, preferably a coarse or fine vacuum, and a high temperature for the removal of the corresponding fatty acid alkyl ester by distillation. Despite the high temperature, however, the heat-sensitive carotene does not undergo any significant decomposition providing evaporators with brief residence times are used. In this way, a carotene yield of 80 to 100% can be obtained in this step of the process.

In one advantageous embodiment of the invention, therefore, the distillation step is carried out in falling film evaporators, in thin-layer evaporators with rotating wipers or in short-path evaporators (molecular evaporators). The evaporation process may be carried out in a single stage. However, it is of advantage to carry out the distillation step in two or more stages and to reduce the pressure from stage to stage. Temperatures in the range from 100 to 250° C. and, more particularly, in the range from 130 to 150° C. are proposed as the distillation temperatures. The operating pressure of the (last) evaporator stage should be in the range from $10^0$ to $10^{-4}$ mbar and, more particularly, in the range from $10^{-1}$ to $10^{-3}$ mbar. Where the evaporation process is carried out in a single stage, these pressures apply to that stage. Where evaporation is carried out in several stages, the operating pressure of the first evaporator stage is advantageously in the range from 1 to 50 mbar and, more particularly, in the range from 2 to 20 mbar.

Depending on the amount of distillate, high concentrations, i.e. up to 20% by weight, of carotene are obtained in the distillation residue.

This residue is saponified in the third step of the process. It is reacted with an alkali metal hydroxide, preferably potassium or sodium hydroxide, under normal pressure and at temperatures of 80° C. to 120° C. Water in up to 5 times the quantity by weight of the distillation residue is preferably added to the reaction mixture either directly or during the saponification reaction in order to improve solubility behavior in the following extraction step.

The fourth and penultimate step of the process comprises extraction of the carotene.

For extraction, the saponified distillation residue is intensively mixed with a solvent mixture which preferably consists of a polar component and a non-polar component. In selecting the solvent mixture, it is important to bear in mind that, on the one hand, the saponified residue or the aqueous soap solution should not be completely soluble whereas, on the other hand, the carotene present in the saponified residue should be readily soluble in the solvent mixture. Linear or branched hydrocarbons containing 4 to 12 carbon atoms are suitable as the non-polar solvent while acetone or tetrahydrofuran is proposed as the polar solvent component. However, other solvents are also possible.

It has surprisingly been found that the carotene can be completely extracted from the saponified distillation residue in only a single extraction step. After the extraction step, a yellow colored lower phase containing soap and water and an orange-red upper phase (extract phase) consisting of the solvents and carotene are obtained.

In the last step of the process, the extract phase is concentrated by evaporation. The solvent is first evaporated off under normal pressure. After about 80 to 95% of the solvent has been removed, the process is preferably continued in a vacuum to achieve complete removal of the solvent.

The temperature of the residue should be kept at a low value during the concentration by evaporation. A temperature of at most 120° C. is proposed for concentration of the extract phase by evaporation and should not be exceeded even on completion of this final step of the process.

The solvent evaporated off is carotene-free and may be reused for extraction. The evaporation residue contains between 20 and 95% by weight of carotene and traces of tocopherols, tocotrienols and sterols.

The carotene obtained by the process according to the invention is suitable for use as a dye and preservative in foods, cosmetics and pharmaceuticals. It may also be used in the prophylaxis of cancer. For making-up, the carotene obtained after the evaporation step may be diluted with suitable oils, for example sunflower oil, to a concentration of 1 to 50% by weight.

The following Example is intended to illustrate the invention without limiting it in any way.

EXAMPLE

In a 5 liter stirred-tank reactor, 3000 g of crude Malaysian palm oil with a carotene content of 900 ppm and an acid value of 9.3 were reacted with 1200 g of methanol. 36.5 g of sodium methylate in the form of a 30% solution in methanol were added to saponify the free fatty acids and as catalyst. The reaction was carried out with stirring under normal pressure at 60° C. After a reaction time of 1 hour, the stirrer was switched off so that the separation of methyl ester phase and glycerol phase began. After a settling time of 2 hours, the glycerol phase was decanted off. The methyl ester phase produced weighed 2719 g and contained 1000 ppm of carotene.

The methyl ester was then removed by distillation in two stages. A rotary evaporator was used for the first stage and a short-path evaporator for the second stage. The first distillation step was started at 100° C./normal pressure. During the distillation process, the pressure was first reduced to 3 mbar and the temperature subsequently increased to 140° C. The quantity of distillate amounted to 2403 g. The distillate was carotene-free and water-clear. The quantity of residue amounted to 304 g. The residue was further concentrated in a short-path evaporator at 160° C./$1.5 \cdot 10^{-2}$ mbar, 226 g of yellowish colored methyl ester being obtained as distillate and 70.3 g with a carotene content of 3.6% as residue.

210 g of water and 17 g of 50% sodium hydroxide were added to the residue, followed by refluxing for 4 hours at 105° C./normal pressure. 295 g of soap solution were produced.

590 g of a solvent mixture of 1 part of n-hexane and 2 parts of acetone were added to this soap solution, followed by stirring for 30 minutes. After a settling time of 2 hours, 542 g of a brown colored lower phase were decanted off. The upper phase obtained weighed 341 g and contained 0.75% of carotene. This upper phase was then concentrated by evaporation, initially under normal pressure and at a temperature of the heating medium of 80° C. In the further course of the evaporation process, the pressure was lowered to 30 mbar and the temperature of the heating medium increased to 120° C. 4.5 g of a dark-red solid with a carotene content of 54.1% were obtained. Accordingly, the carotene yield of the process as a whole is 90%. The material produced can be made up without any further treatment for use in foods, cosmetics or pharmaceuticals.

We claim:

1. A process for recovering a carotene from an oil that contains carotenes and free fatty acids comprising the steps of:
   a) transesterifying the oil with an alkanol having up to 4 carbon atoms to form a two-phase mixture comprising a glycerol phase and an ester phase, said ester phase comprising fatty acid esters and the carotene;
   b) separating the fatty acid esters from the ester phase by distillation or evaporation to form a residue containing the carotene;
   c) saponifying the residue with an alkali metal hydroxide;
   d) extracting the carotene from the saponified residue with an organic solvent to form an extract phase containing the carotene; and
   e) removing the solvent from the extract phase by evaporation.

2. A process according to claim 1, wherein the oil is palm oil.

3. A process according to claim 1, wherein prior to the transesterification step, the free fatty acids of the oil are esterified.

4. A process according to claim 1, wherein the transesterification is carried out with an amount of an alkaline catalyst sufficient to saponify the free fatty acids of the oil.

5. A process according to claim 3, wherein the transesterification is carried out in the presence of a homogeneous alkaline catalyst.

6. A process according to claim 5, wherein the catalyst is sodium hydroxide, potassium hydroxide, sodium methylate, or potassium methylate.

7. A process according to claim 1, wherein the temperature of the transesterification is 30° C. to 110° C.

8. A process according to claim 7, wherein the temperature of the transesterification is 30° C. to 100° C.

9. A process according to claim 8, wherein the temperature of the transesterification is 50° C. to 70° C.

10. A process according to claim 1, wherein the time of the transesterification is 10 minutes to 180 minutes.

11. A process according to claim 10, wherein the time of the transesterification is 30 minutes to 90 minutes.

12. A process according to claim 1, wherein the separation step removes from the ester phase 70% to 99.5% by weight of the fatty acid esters formed in the transesterification step.

13. A process according to claim 12, wherein the separation step removes from the ester phase 95% to 99% by weight of the fatty acid esters formed in the transesterification step.

14. A process according to claim 1, wherein the separation step is carried out in a falling film evaporator, a wipe film evaporator, or a molecular evaporator.

15. A process according to claim 1, wherein the distillation is carried out at a temperature of 100° C. to 250° C.

16. A process according to claim 15, wherein the distillation is carried out at a temperature of 130° C. to 150° C.

17. A process according to claim 1, wherein the separation step comprises distillation and is carried out in more than one stage wherein the distillation pressure is reduced from stage to stage.

18. A process according to claim 17, wherein the pressure in the final distillation stage is $10^0$ mbar to $10^{-4}$ mbar.

19. A process according to claim 18, wherein the pressure in the final distillation stage is $10^{-1}$ mbar to $10^{-3}$ mbar.

20. A process according to claim 17, wherein the pressure in the first distillation stage is 1 mbar to 50 mbar.

21. A process according to claim 20, wherein the pressure in the first distillation stage is 2 to 20 mbar.

22. A process according to claim 1, wherein the saponification step is carried out at a temperature of 80° C. to 120° C.

23. A process according to claim 1, wherein for the saponification step the residue is diluted with up to five times by weight of water, based on the weight of the residue.

24. A process for recovering carotene from an oil that contains carotene and free fatty acids comprising the steps of:

a) transesterifying the oil in the presence of an alkaline catalyst selected from the group consisting of sodium hydroxide, potassium hydroxide, sodium methylate, and potassium methylate with an alkanol selected from the group consisting of methanol, ethanol, n-propanol, isopropanol, n-butanol, or isobutanol at a temperature of 30° C. to 110° C. for 10 minutes to 180 minutes to form a two-phase mixture comprising a glycerol phase and an ester phase comprising fatty acid esters and the carotene;

b) distilling the ester phase at a temperature of 100° C. to 250° C. and a pressure of $10^0$ mbar to $10^{-4}$ mbar to separate 70% to 99.5% by weight of the esters obtained in the transesterification step from the ester phase and to form a residue containing the carotene;

c) diluting the residue with up to 5 times by weight of water based on the weight of residue;

d) saponifying the residue with an alkali metal hydroxide at a temperature of 80° C. to 120° C.;

e) extracting the carotene from the saponified residue with a solvent mixture comprising a component and a nonpolar component to form an extract phase containing the carotene; and f) removing the solvent from the extract phase by evaporation.

25. A process for recovering carotene from an oil that contains carotene and free fatty acids comprising the steps of:

a) transesterifying the oil in the presence of an alkaline catalyst selected from the group consisting of sodium hydroxide, potassium hydroxide, sodium methylate, and potassium methylate with an alkanol selected from the group consisting of methanol, ethanol, n-propanol, isopropanol, n-butanol, or isobutanol at a temperature of 50° C. to 70° C. for 30 minutes to 90 minutes to form a two-phase mixture comprising a glycerol phase and an ester phase comprising fatty acid esters and the carotene;

b) distilling the ester phase at a temperature of 130° C. to 150° C. and a pressure of $10^{-1}$ mbar to $10^{-3}$ mbar to separate 95% to 99% by weight of the esters obtained in the transesterification step from the ester phase and to form a residue containing the carotene;

c) diluting the residue with up to 5 times by weight of water based on the weight of residue;

d) saponifying the residue with an alkali metal hydroxide at a temperature of 80° C. to 120° C.;

e) extracting the carotene from the saponified residue with a solvent mixture comprising a nonpolar solvent selected from the group consisting of linear or branched hydrocarbons containing 4 to 12 carbon atoms and a polar solvent selected from the group consisting of acetone and tetrahydrofuran to form an extract phase containing the carotene; and f) separating the solvents from the extract phase to form an evaporation residue comprising 20% to 95% by weight carotene.

* * * * *